(12) United States Patent
Rafiee

(10) Patent No.: US 10,449,046 B2
(45) Date of Patent: Oct. 22, 2019

(54) DEVICES, SYSTEMS AND METHODS FOR REPAIRING LUMENAL SYSTEMS

(71) Applicant: MEHR MEDICAL LLC, Andover, MA (US)

(72) Inventor: Nasser Rafiee, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 761 days.

(21) Appl. No.: 14/453,478

(22) Filed: Aug. 6, 2014

(65) Prior Publication Data

US 2015/0039083 A1  Feb. 5, 2015

Related U.S. Application Data

(63) Continuation of application No. PCT/US2014/049629, filed on Aug. 4, 2014.

(60) Provisional application No. 61/862,041, filed on Aug. 4, 2013, provisional application No. 61/878,264, filed on Sep. 16, 2013, provisional application No. 62/007,369, filed on Jun. 3, 2014.

(51) Int. Cl.
| | | |
|---|---|---|
| *A61F 2/24* | (2006.01) | |
| *A61B 17/04* | (2006.01) | |
| *A61B 17/064* | (2006.01) | |
| *A61B 17/22* | (2006.01) | |

(52) U.S. Cl.
CPC ........ *A61F 2/2436* (2013.01); *A61B 17/0401* (2013.01); *A61F 2/2409* (2013.01); *A61F 2/2418* (2013.01); *A61F 2/2454* (2013.01); *A61F 2/2457* (2013.01); *A61B 2017/0409* (2013.01); *A61B 2017/0441* (2013.01); *A61B 2017/0649* (2013.01); *A61B 2017/22068* (2013.01); *A61F 2220/0008* (2013.01); *A61F 2250/0003* (2013.01)

(58) Field of Classification Search
CPC ........ A61F 2/24; A61F 2/2409; A61F 2/2445; A61F 2/2418; A61F 2/848; A61F 2220/0008; A61F 2220/0016; A61F 2220/8486; A61F 2220/8483; A61F 2/2439; A61B 2017/0649
USPC .............................. 623/2.1, 2.11, 2.18, 1.11
See application file for complete search history.

(56) References Cited

U.S. PATENT DOCUMENTS

| | | | |
|---|---|---|---|
| 4,106,129 | A | 8/1978 | Carpentier et al. |
| 4,259,753 | A | 4/1981 | Liotta et al. |
| 4,666,442 | A | 5/1987 | Arru et al. |
| 4,692,164 | A | 9/1987 | Dzemeshkevich et al. |

(Continued)

FOREIGN PATENT DOCUMENTS

| | | |
|---|---|---|
| EP | 2412397 A1 | 2/2012 |
| RU | 100 718 U1 | 12/2010 |

(Continued)

OTHER PUBLICATIONS

International Search Report, for related application No. PCT/US2011/059586, dated May 25, 2012.

(Continued)

*Primary Examiner* — Diane D Yabut
*Assistant Examiner* — Majid Jamialahmadi
(74) *Attorney, Agent, or Firm* — Crawford Maunu PLLC

(57) ABSTRACT

The disclosure provides systems and related methods for delivering a prosthesis to a target location. Various embodiments of useful valve prostheses are also disclosed.

20 Claims, 15 Drawing Sheets

(56) References Cited

U.S. PATENT DOCUMENTS

| | | |
|---|---|---|
| 5,411,552 A | 5/1995 | Andersen et al. |
| 5,449,384 A | 9/1995 | Johnson |
| 5,606,928 A | 3/1997 | Religa et al. |
| 5,788,715 A | 8/1998 | Watson, Jr. et al. |
| 5,843,167 A * | 12/1998 | Dwyer .................. A61F 2/07 623/1.14 |
| 5,861,028 A | 1/1999 | Angell |
| 5,895,410 A | 4/1999 | Forber et al. |
| 5,928,281 A | 7/1999 | Huynh et al. |
| 6,059,769 A | 5/2000 | Lunn et al. |
| 6,106,510 A | 8/2000 | Lunn et al. |
| 6,375,774 B1 | 4/2002 | Lunn et al. |
| 6,599,303 B1 | 7/2003 | Peterson |
| 6,602,271 B2 | 8/2003 | Adams et al. |
| 6,716,231 B1 | 4/2004 | Rafiee et al. |
| 6,733,525 B2 | 5/2004 | Yang et al. |
| 6,790,229 B1 | 9/2004 | Berreklouw |
| 6,797,000 B2 | 9/2004 | Simpson et al. |
| 6,800,081 B2 | 10/2004 | Parodi |
| 6,866,677 B2 | 3/2005 | Douk et al. |
| 6,911,036 B2 | 6/2005 | Douk et al. |
| 6,953,476 B1 | 10/2005 | Shalev |
| 6,960,217 B2 | 11/2005 | Bolduc |
| 7,044,958 B2 | 5/2006 | Douk et al. |
| 7,066,946 B2 | 6/2006 | Douk et al. |
| 7,189,259 B2 | 3/2007 | Simionescu et al. |
| 7,195,641 B2 | 3/2007 | Palmaz et al. |
| 7,201,772 B2 | 4/2007 | Schwammenthal et al. |
| 7,294,135 B2 | 11/2007 | Stephens et al. |
| 7,316,706 B2 | 1/2008 | Bloom et al. |
| 7,399,315 B2 | 7/2008 | Iobbi |
| 7,425,219 B2 | 9/2008 | Quadri |
| 7,442,204 B2 | 10/2008 | Schwammenthal et al. |
| 7,442,207 B2 | 10/2008 | Rafiee |
| 7,445,631 B2 | 11/2008 | Salahieh et al. |
| 7,481,838 B2 | 1/2009 | Carpentier et al. |
| 7,491,232 B2 | 2/2009 | Bolduc et al. |
| 7,524,330 B2 | 4/2009 | Berreklouw |
| 7,655,040 B2 | 2/2010 | Douk et al. |
| 7,682,352 B2 | 3/2010 | Rafiee et al. |
| 7,699,892 B2 | 4/2010 | Rafiee et al. |
| 7,716,801 B2 | 5/2010 | Douk et al. |
| 7,753,840 B2 | 7/2010 | Simionescu et al. |
| 7,753,949 B2 | 7/2010 | Lamphere et al. |
| 7,780,726 B2 | 8/2010 | Seguin |
| 7,799,069 B2 | 9/2010 | Bailey et al. |
| 7,806,917 B2 | 10/2010 | Xiao |
| 7,806,919 B2 | 10/2010 | Bloom et al. |
| 7,815,673 B2 | 10/2010 | Bloom et al. |
| 7,947,072 B2 | 5/2011 | Yang et al. |
| 7,955,384 B2 | 6/2011 | Rafiee et al. |
| 7,972,370 B2 | 7/2011 | Douk et al. |
| 7,998,188 B2 | 8/2011 | Zilla et al. |
| 8,002,825 B2 | 8/2011 | Letac et al. |
| 8,052,750 B2 | 11/2011 | Tuval et al. |
| 8,062,355 B2 | 11/2011 | Figulla et al. |
| 8,070,802 B2 | 12/2011 | Lamphere et al. |
| 8,092,518 B2 | 1/2012 | Schreck |
| 8,092,520 B2 | 1/2012 | Quadri |
| 8,092,524 B2 | 1/2012 | Nugent et al. |
| 8,226,710 B2 | 7/2012 | Nguyen et al. |
| 8,252,051 B2 | 8/2012 | Chau et al. |
| 8,308,798 B2 | 11/2012 | Pintor et al. |
| 8,337,541 B2 | 12/2012 | Quadri et al. |
| 8,348,995 B2 | 1/2013 | Tuval et al. |
| 8,348,996 B2 | 1/2013 | Tuval et al. |
| 8,353,954 B2 | 1/2013 | Cai et al. |
| 8,353,955 B2 | 1/2013 | Styrc et al. |
| 2001/0021872 A1 | 9/2001 | Bailey et al. |
| 2002/0032481 A1 | 3/2002 | Gabbay |
| 2002/0138138 A1 | 9/2002 | Yang |
| 2003/0055495 A1 | 3/2003 | Pease et al. |
| 2003/0065386 A1 | 4/2003 | Weadock |
| 2003/0097172 A1 | 5/2003 | Shalev et al. |
| 2004/0087998 A1 | 5/2004 | Lee et al. |
| 2004/0127916 A1 | 7/2004 | Bolduc et al. |
| 2005/0038508 A1 | 2/2005 | Gabbay |
| 2005/0043790 A1 | 2/2005 | Seguin |
| 2005/0055082 A1 | 3/2005 | Ben-Muvhar et al. |
| 2005/0137769 A1 | 6/2005 | Salahieh et al. |
| 2005/0143809 A1 | 6/2005 | Salahieh et al. |
| 2005/0177180 A1 | 8/2005 | Kaganov et al. |
| 2005/0288706 A1 | 12/2005 | Widomski et al. |
| 2006/0085012 A1 | 4/2006 | Dolan |
| 2006/0106449 A1 | 5/2006 | Ben-Muvhar |
| 2006/0106450 A1 | 5/2006 | Ben-Muvhar |
| 2006/0173537 A1 | 8/2006 | Yang et al. |
| 2007/0043435 A1 | 2/2007 | Seguin et al. |
| 2007/0067029 A1 | 3/2007 | Gabbay |
| 2007/0250160 A1 | 10/2007 | Rafiee |
| 2007/0255398 A1 | 11/2007 | Yang et al. |
| 2007/0288089 A1 | 12/2007 | Gurskis et al. |
| 2007/0293942 A1 | 12/2007 | Mizraee |
| 2008/0015687 A1 | 1/2008 | Lashinski et al. |
| 2008/0021537 A1 | 1/2008 | Ben-Muvhar et al. |
| 2008/0065191 A1 | 3/2008 | Bolduc et al. |
| 2008/0071369 A1 * | 3/2008 | Tuval .................. A61F 2/2418 623/2.38 |
| 2008/0077234 A1 | 3/2008 | Styrc |
| 2008/0125860 A1 | 5/2008 | Webler et al. |
| 2008/0208328 A1 | 8/2008 | Antocci et al. |
| 2008/0221672 A1 | 9/2008 | Lamphere et al. |
| 2009/0005863 A1 | 1/2009 | Goetz et al. |
| 2009/0062841 A1 | 3/2009 | Amplatz et al. |
| 2009/0270966 A1 | 10/2009 | Douk et al. |
| 2009/0270976 A1 | 10/2009 | Douk et al. |
| 2009/0306768 A1 | 12/2009 | Quadri |
| 2009/0319038 A1 | 12/2009 | Gurskis et al. |
| 2010/0036479 A1 | 2/2010 | Hill et al. |
| 2010/0082094 A1 | 4/2010 | Quadri et al. |
| 2010/0100167 A1 | 4/2010 | Bortlein et al. |
| 2010/0174363 A1 | 7/2010 | Castro |
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0249923 A1 | 9/2010 | Alkhatib et al. |
| 2010/0262232 A1 | 10/2010 | Annest |
| 2010/0280606 A1 | 11/2010 | Naor |
| 2010/0298931 A1 | 11/2010 | Quadri et al. |
| 2011/0112632 A1 | 5/2011 | Chau et al. |
| 2011/0137409 A1 | 6/2011 | Yang et al. |
| 2011/0172784 A1 | 7/2011 | Richter et al. |
| 2011/0282438 A1 | 11/2011 | Drews et al. |
| 2011/0313515 A1 | 12/2011 | Quadri et al. |
| 2011/0319988 A1 | 12/2011 | Schankereli et al. |
| 2011/0319989 A1 * | 12/2011 | Lane .................. A61F 2/2418 623/2.11 |
| 2011/0319990 A1 * | 12/2011 | Macoviak ............. A61F 2/2445 623/2.11 |
| 2012/0022639 A1 | 1/2012 | Hacohen |
| 2012/0059450 A1 | 3/2012 | Chiang et al. |
| 2012/0078353 A1 | 3/2012 | Quadri et al. |
| 2012/0078360 A1 | 3/2012 | Rafiee |
| 2012/0179086 A1 * | 7/2012 | Shank .................. A61F 2/04 604/8 |
| 2012/0179244 A1 | 7/2012 | Schankereli et al. |
| 2012/0215303 A1 | 8/2012 | Quadri et al. |
| 2012/0316642 A1 | 12/2012 | Yu et al. |
| 2012/0323316 A1 | 12/2012 | Chau et al. |
| 2014/0018906 A1 | 1/2014 | Rafiee |
| 2014/0128965 A1 | 5/2014 | Rafiee |
| 2014/0163668 A1 | 6/2014 | Rafiee |
| 2014/0324164 A1 * | 10/2014 | Gross .................. A61F 2/2409 623/2.37 |
| 2014/0358223 A1 | 12/2014 | Rafiee et al. |
| 2014/0379074 A1 * | 12/2014 | Spence .................. A61F 2/2418 623/2.11 |
| 2014/0039083 A1 | 2/2015 | Rafiee |

FOREIGN PATENT DOCUMENTS

| | | |
|---|---|---|
| WO | WO2007121314 A2 | 10/2007 |
| WO | WO2012061809 A2 | 5/2012 |

(56) References Cited

FOREIGN PATENT DOCUMENTS

| WO | WO2013131069 A1 | 9/2013 |
| WO | WO2015069947 A1 | 5/2015 |
| WO | WO2015148821 A1 | 10/2015 |

OTHER PUBLICATIONS

International Preliminary Report on Patentability and Written Opinion, or related application No. PCT/US2011/059586, dated May 25, 2012.
BioIntegral Surgical, Mitral Valve Restoration System.
International Search Report for co-pending international application No. PCT/US2013/028774, dated Jun. 14, 2013.
International Preliminary Report on Patentability and Written Opinion, on related application No. PCT/US2014/064431 dated Mar. 26, 2015.
International Search Report, for related application No. PCT/US2015/022782, dated Jun. 18, 2015.

\* cited by examiner

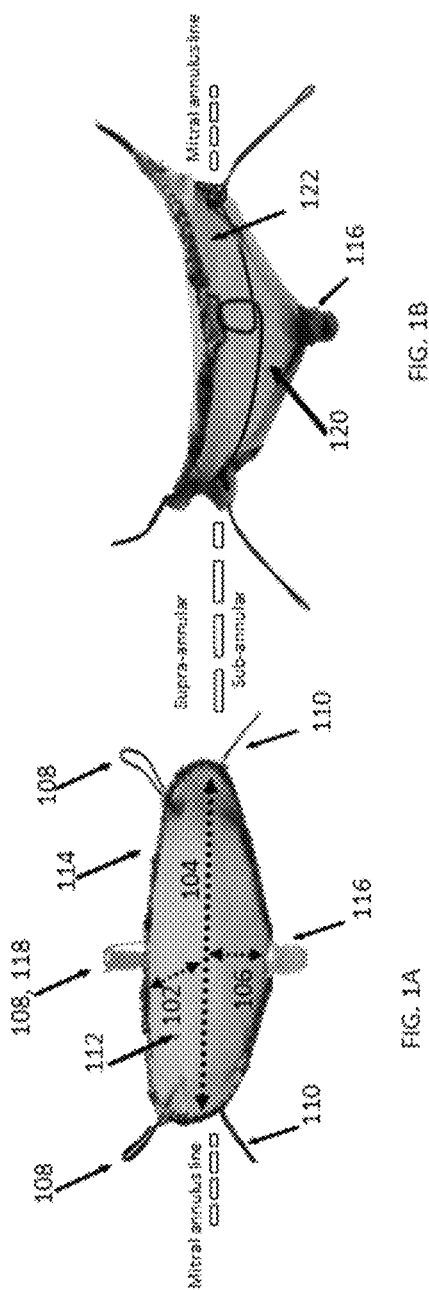

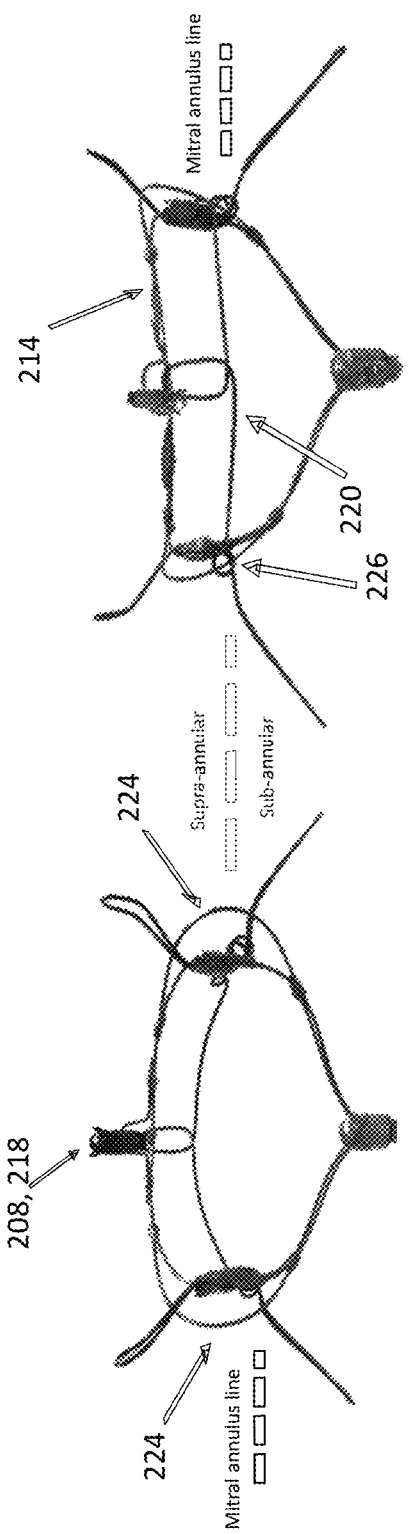

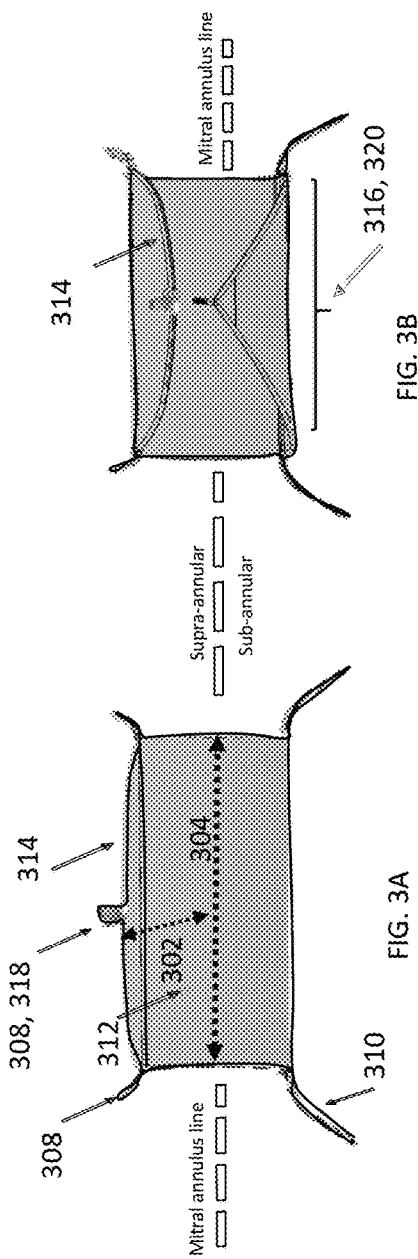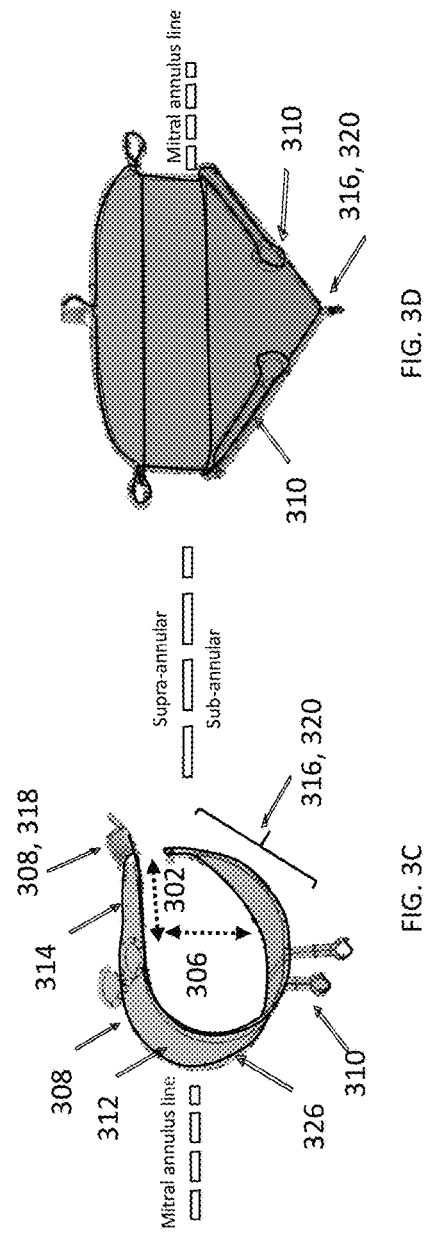

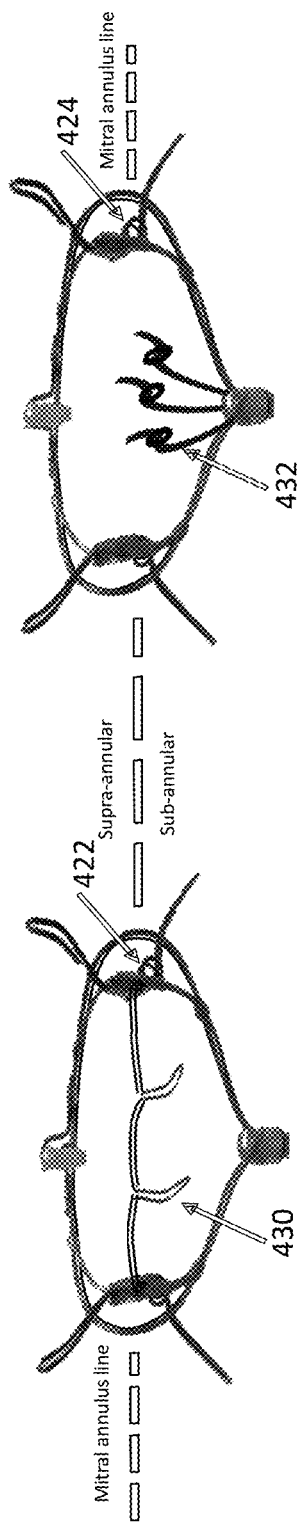

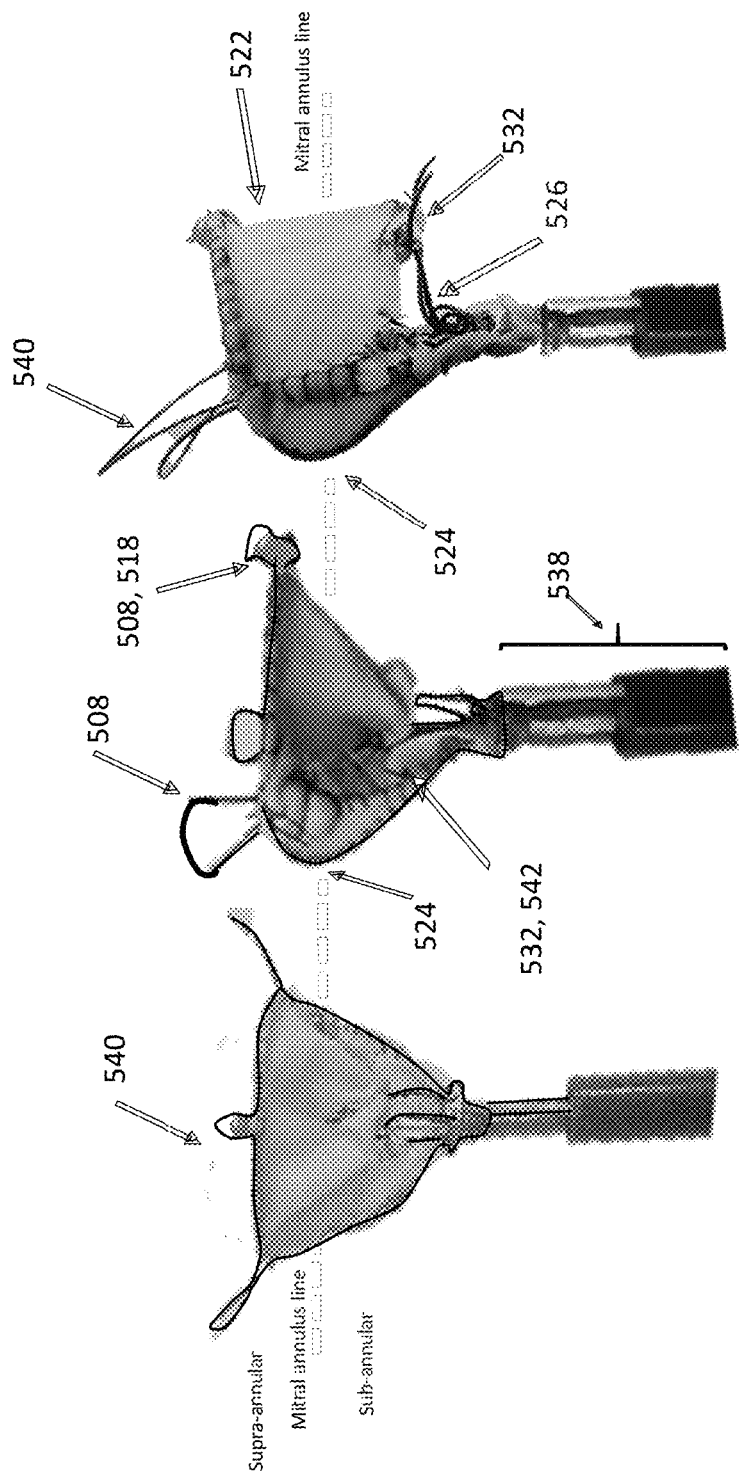

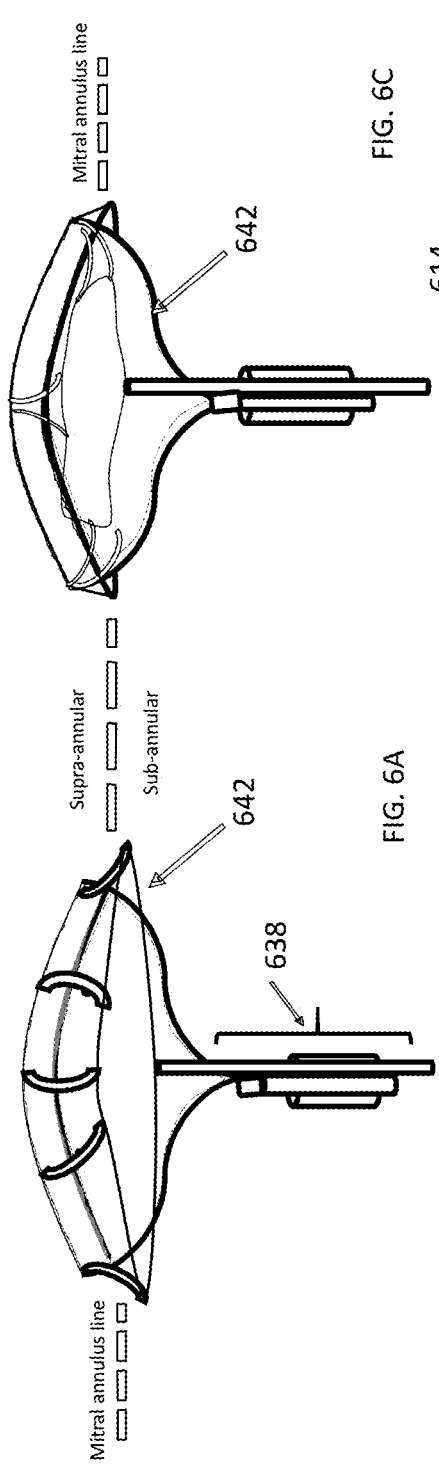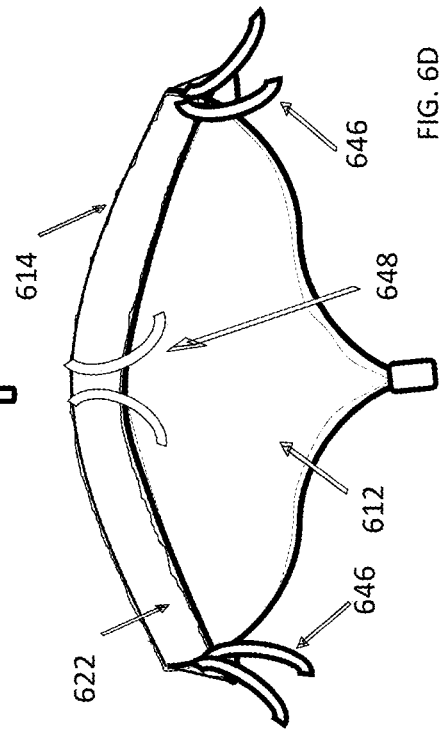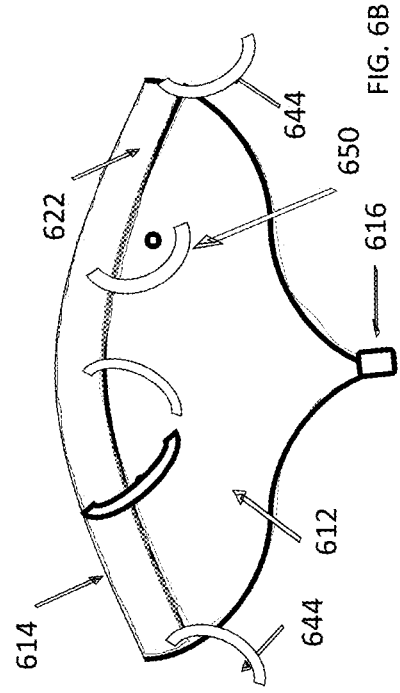

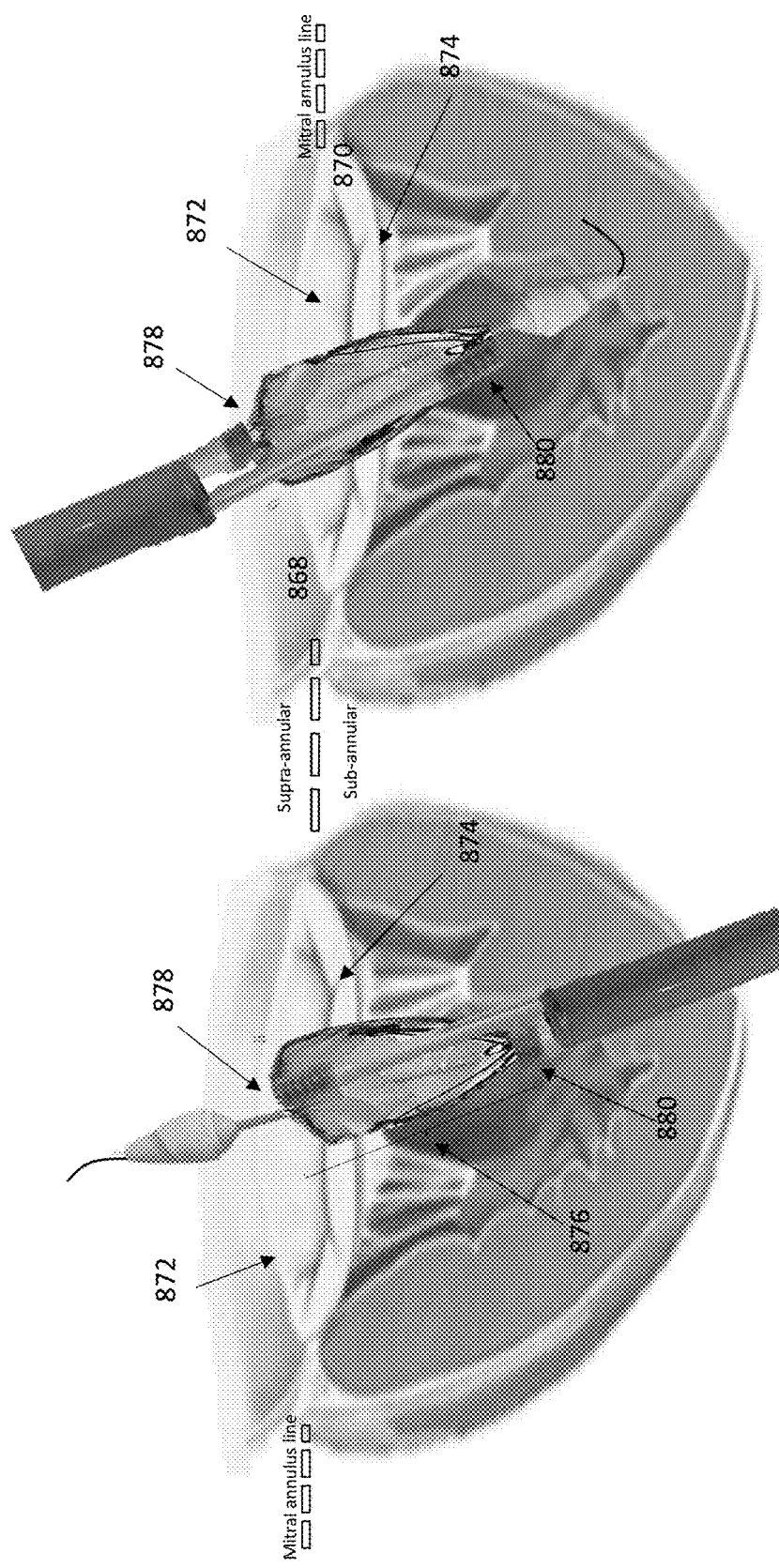

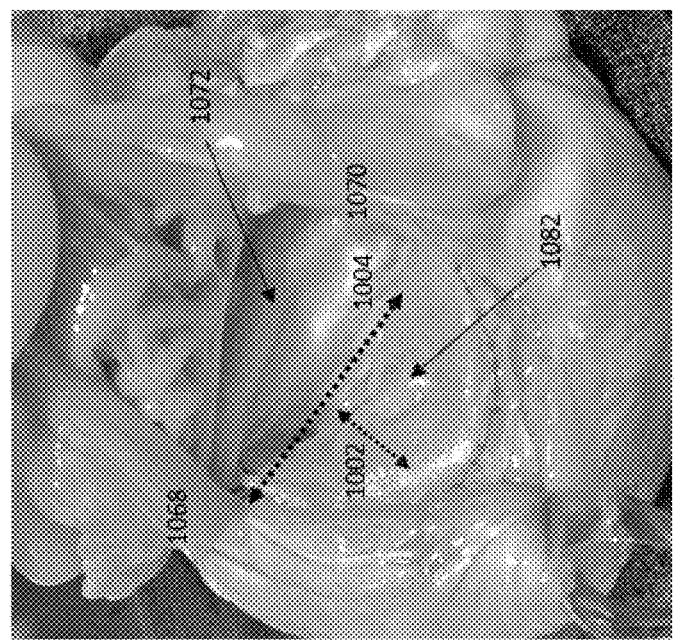
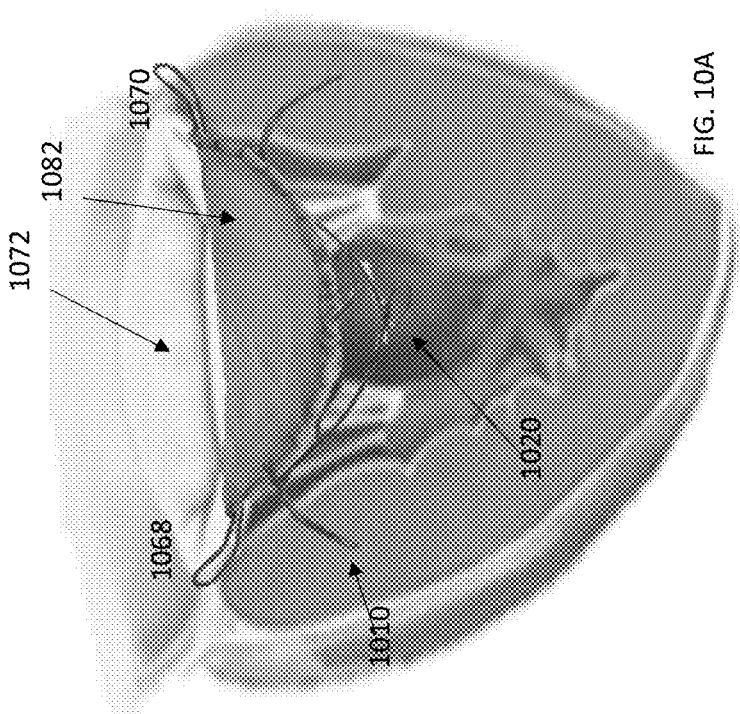

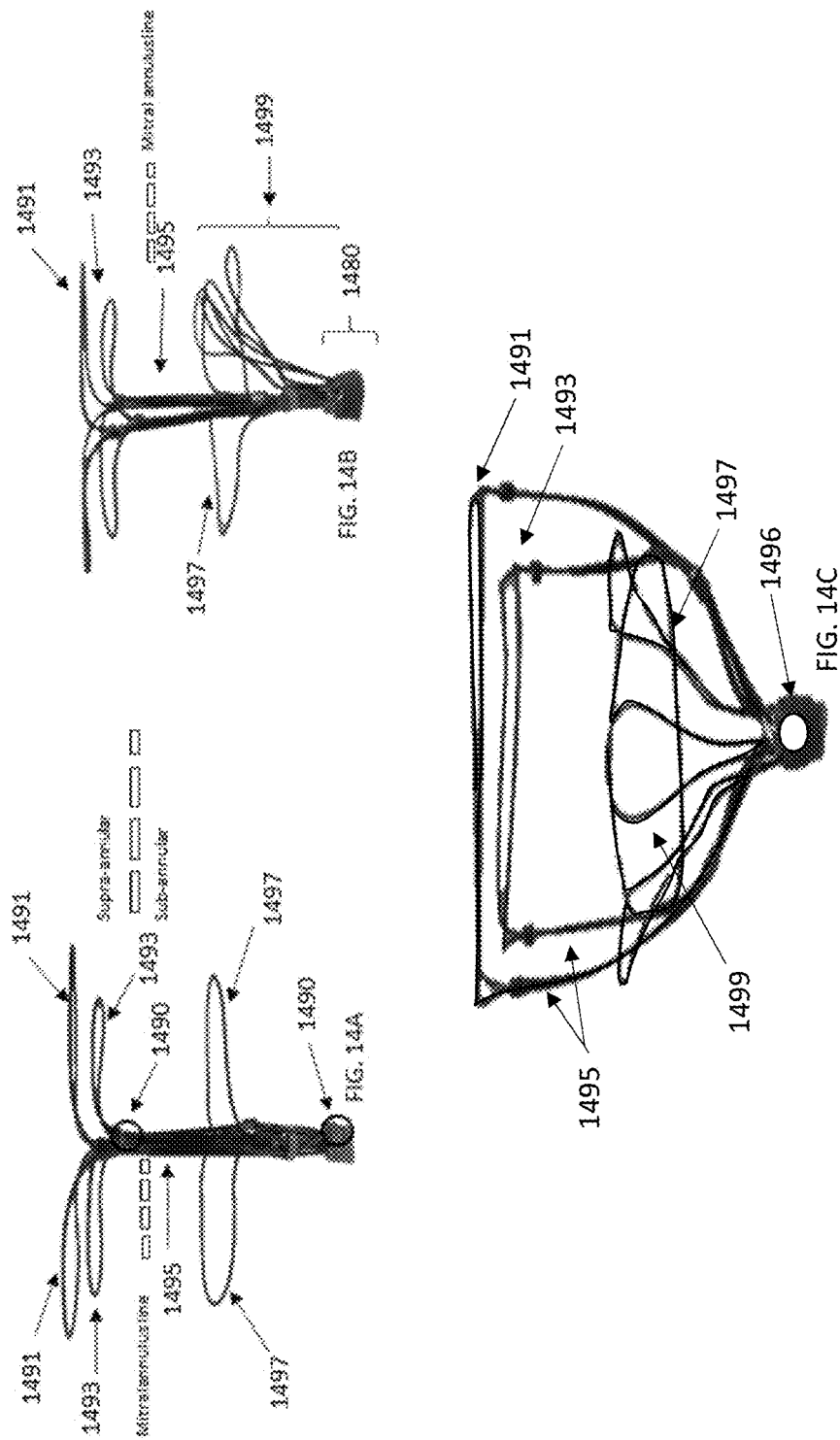

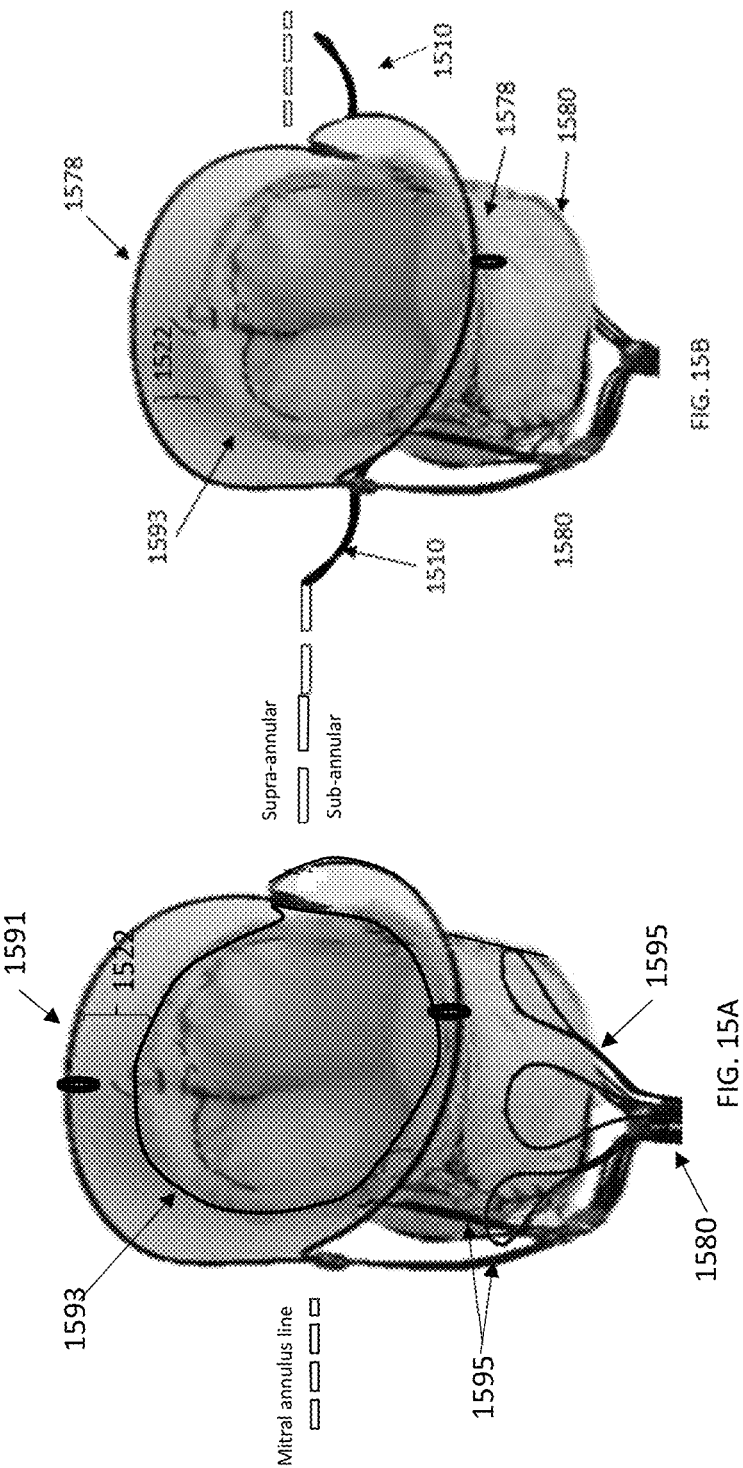

DEVICES, SYSTEMS AND METHODS FOR REPAIRING LUMENAL SYSTEMS

CROSS-REFERENCE TO RELATED APPLICATIONS

This patent application claims the benefit of priority to International Application No. PCT/US2014/49629, filed Aug. 4, 2014, which claims the benefit of priority to U.S. Provisional Patent Application Ser. No. 61/862,041, filed Aug. 4, 2013, U.S. Provisional Patent Application Ser. No. 61/878,264, filed Sep. 16, 2013 and U.S. Provisional Patent Application Ser. No. 62/007,369, filed Jun. 3, 2014. This application is also related to U.S. patent application Ser. No. 14/074,517 filed Nov. 7, 2013 which in turn claims the benefit of U.S. Provisional Patent Application Ser. No. 61/723,734, filed Nov. 7, 2012, U.S. patent application Ser. No. 13/240,793, filed Sep. 22, 2011, International Application No. PCT/US2013/28774, filed Mar. 2, 2013, International Application No. PCT/US2011/59586, filed Nov. 7, 2011. The entire contents of each of the above referenced patent applications is incorporated herein by reference for any purpose whatsoever.

BACKGROUND

Heart valves permit unidirectional flow of blood through the cardiac chambers to permit the heart to function as a pump. Valvular stenosis is one form of valvular heart disease that prevents blood from flowing through a heart valve, ultimately causing clinically significant heart failure in humans. Another form of valvular disease results from heart valves becoming incompetent. Failure of adequate heart valve closure permits blood to leak through the valve in the opposite direction to normal flow. Such reversal of flow through incompetent heart valves can cause heart failure in humans.

The human mitral valve is a complicated structure affected by a number of pathological processes that ultimately result in valvular incompetence and heart failure in humans. Components of the mitral valve include the left ventricle, left atrium, anterior and posterior papillary muscles, mitral annulus, anterior mitral leaflet, posterior mitral leaflet and numerous chordae tendonae. The anterior leaflet occupies roughly ⅔ of the mitral valve area whereas the smaller posterior leaflet occupies ⅓ of the area. The anterior mitral leaflet, however, hangs from the anterior ⅓ of the perimeter of the mitral annulus whereas the posterior mitral leaflet occupies ⅔ of the annulus circumference. Furthermore, the posterior mitral leaflet is often anatomically composed of three separate segments. In diastole, the anterior leaflet and the three posterior leaflets are pushed into the left ventricle opening. In systole, the leaflets are pushed toward the plane of the mitral annulus where the posterior leaflets and larger anterior leaflet come into coaptation to prevent blood flow from the left ventricle to the left atrium. The leaflets are held in this closed position by the chordae tendonae. Dysfunction or failure of one or more of these mitral components may cause significant mitral valvular regurgitation and clinical disease in humans.

Surgical treatment has been the gold standard since its introduction in the 1950s. Currently, there are two surgical options offered for treatment. The first, mitral valve replacement, requires complex surgery using cardiopulmonary bypass to replace the mitral valve using a mechanical or bioprosthetic valvular prosthesis. Although a time-tested and proven strategy for treatment, bioprostheic valves suffer from poor long-term durability and mechanical valves require anticoagulation. As an alternative, surgical mitral valve repair has emerged as a superior procedure to achieve mitral valve competence and normal function. This operation is really a collection of surgical techniques and prostheses that collectively are referred to a mitral valve repair. Each component of the mitral valve can be altered, replaced, repositioned, resected or reinforced to achieve mitral valve competence.

Mitral annuloplasty has become a standard component of surgical mitral valve repair. In performing this procedure, the circumference of the mitral valve annulus is reduced and/or reshaped by sewing or fixing a prosthetic ring or partial ring to the native mitral valve annulus. As a consequence of mitral annuloplasty, the posterior mitral leaflet often becomes fixed in a closed position, pinned against the posterior left ventricular endocardium. The opening and closure of the mitral valve is subsequently based almost entirely on the opening and closing of the anterior mitral valve leaflet.

SUMMARY

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

To achieve these and other advantages and in accordance with the purpose of the disclosure, as embodied herein, in one aspect, the disclosure includes embodiments of a heart valve prosthesis. The prosthesis is configured to achieve inter-commissural self-alignment. It is preferably configured to automatically self-orient rotationally based on the native mitral commissures substantially about a central axis perpendicular to a plane substantially defined by the mitral annulus to simplify implantation. The inter-commissural self-alignment outward expansion naturally orients the prosthesis along the inter-commissural line and serves as the primary source of fixation. Accordingly, it is possible to achieve stentless and anchor-free fixation without apical tethering or a bulky sub-valvular prosthesis. Moreover, the prosthesis can be repositioned during and after delivery, and if required, can be completely retrieved even after deployment. The posterior-only embodiments create a non-regurgitant line of coaptation in coordination with a patient's native anterior mitral leaflet. This allows the treated valve to accommodate a range of loading conditions. The prosthesis additionally avoids left ventricular outflow obstruction, and is also amenable to retrograde and antegrade delivery. The leaflet(s) of the prosthesis include no free ends, rendering them less thrombogenic and less prone to failure. Moreover, the prosthesis geometry causes less flow agitation during ejection.

In some embodiments, prostheses are provided including left ventricular ("LV") sub annulus anchors for deploying under the mitral annulus in the left ventricle. The framework for the prostheses can be made from a variety of materials, but are preferably made from a nickel-titanium alloy (NiTi). The deployable anchors can be NiTi loop frames attached to the main frame of the device by any desired technique. Preferably, coil-shaped stress relief loops are additionally provided bent into the wireframe forming the anchors and/or main frame of the prosthesis to permit the anchors to be fully collapsed without risk of fracture of the NiTi material. In some implementations, one or more such NiTi self expanding anchors are located proximate each commissure and along the posterior periphery of the implant. One or more (and sometimes all) of the collapsible NiTi ventricular anchors are held in a collapsed condition prior to and during deployment by a controllable tether threaded through the wire loop and/or stress loop and/or additional eyelet of each anchor. Prior to loading into the prosthesis delivery system, the LV anchors are all pulled together toward a central elongate axis defined by the delivery system by the controllable tether and locked at the back (proximal) end of the delivery system. The prosthesis is then radially compressed (in some cases partially due to stretching it along the axis of the delivery system and loaded into the delivery system. The delivery system can then be advanced to the mitral region either percutaneously via the Left Atrium ("LA") or transapically via the left ventricle. In some embodiments, the LV anchors are covered with tissue or other membrane to help facilitate prevention of paravalvular leaks.

All prostheses disclosed herein can also be provided with an atrial expansion loop for seating in the left atrium and extending around the entire periphery of the atrium as described in International Patent Application No. PCT/US2013/028774, filed Mar. 2, 2013, which is incorporated by reference herein above.

In accordance with further implementations, the prostheses described herein can be used with active rail fixation techniques such as those described in U.S. patent application Ser. No. 14/074,517 filed Nov. 7, 2013 and International Application No. PCT/US2011/59586, filed Nov. 7, 2011 which are both incorporated by reference herein above. For example, rail anchors can be positioned proximate the middle of the native posterior mitral sub-annulus and/or one at each commissure or attached along the posterior leaflets. The rail tether can be pre-loaded through one or more guide eyelets or loops formed into or onto the prosthesis when initially loading the delivery system. The prosthesis can then be delivered over the tethers and the prosthesis can be locked into place. The tethers can be cut and the delivery system can accordingly be removed. Any rail delivery technique described or incorporated by reference herein can be used on any partial or full mitral or tricuspid valvular prosthesis described herein or incorporated herein by reference.

In some embodiments, the disclosure provides a heart valve prosthesis, including a first framework of a plurality semi-circular members adapted to deploy from the distal end of a first shaft within a catheter to occupy a majority of the circumference substantially coinciding with the circumferential extent of a native posterior mitral leaflet above the mitral valve annulus in the left atrium. A first semi-circular member is adapted to exert an outward radial force above the anterior annulus against the left atrium to fix the heart valve prosthesis in the desired position. A second semi-circular member is configured to exert an outward radial force above a posterior region of the mitral annulus (posterior to the mitral valve commissures) to fix the heart valve prosthesis in position. The first and second semi-circular members are configured to be joined to a main body of the prosthesis at their terminal ends. Three self expanding vertically oriented adjustable loop anchors can be provided to deploy above the mitral annulus to prevent the prosthesis from migrating to the LV, and to ensure proper positioning of the prosthesis so that the native anterior leaflet properly closes against the prosthesis.

In some implementations, the disclosure provides a partial valvular prosthesis for implantation over a native mitral valve. The prosthesis includes a main circumferential frame having a supra annular frame portion for resting above the mitral annulus over a native posterior mitral leaflet and a sub annular frame portion for extending downwardly into a native left ventricle. The main circumferential frame is preferably substantially covered by a curved membrane. The prosthesis also includes at least one deployable anchor attached to the main circumferential frame, the deployable anchor having a body formed from a wire material including at least one stress coil having at least one turn, the at least one stress coil being configured to urge the anchor outwardly to help hold the prosthesis in place upon deployment into a native mitral location.

If desired, the at least one deployable anchor can be configured to deploy against a portion of a native left ventricular site. The prosthesis can include at least two deployable anchors including at least one stress coil having at least one turn that are configured to self-expand against the left ventricle to help hold the prosthesis in place. In some embodiments, the prosthesis includes three deployable anchors, each including at least one stress coil having at least one turn that are configured to self-expand against the left ventricle to help hold the prosthesis in place. If desired, two of the aforementioned anchors can be configured to self expand laterally intro the ventricle near the middle of the mitral annulus, and the third anchor can be configured to self expand to a location underneath a central region of the posterior mitral annulus.

In another implementation, a third anchor can be formed into the main frame of the prosthesis and is configured to self expand toward a location underneath a central region of the posterior mitral annulus. The membrane can be stretched over the third anchor. The membrane of the prosthesis can define a curved plane that stretches from above the mitral annulus proximate the periphery of the mitral annulus and curves downwardly into the left ventricle and bends upwardly to contact the underside of a central posterior region of the mitral annulus. The main circumferential frame can be formed from at least one perimeter wire loop that traverses the perimeter of the membrane. If desired, the at least one perimeter wire loop can form a saddle shape when the prosthesis is deployed. The main circumferential frame portion can be formed by an outer perimeter structural wire attached to an inner circumferential loop, wherein the at least one deployable anchor is attached to the inner circumferential loop. In various embodiments, the at least one stress coil can be disposed in a sub annular location, or supra annular location, as desired. If desired, the outer perimeter structural wire can extend outwardly laterally beyond the inner loop to form crescent shaped frames on each side of the prosthesis to facilitate positioning of the implant upon installation.

In further embodiments, the prosthesis can further include at least one counter fixation retainer disposed on a supra annular portion of the prosthesis that sits in the left atrium after the prosthesis is implanted in a mitral valve annulus. Preferably, the prosthesis includes a plurality of counter fixation retainers disposed on the prosthesis, wherein at least two of the retainers engage the left atrial wall proximate opposing native commissures and wherein at least one of the retainers engages the left atrial wall proximate a central posterior location of the mitral annulus. If desired, the prosthesis can be configured to expand outwardly toward the commissures during implantation and self-align in the mitral opening. The stress loop(s) can be between about 3 mm in diameter and about 8 mm in outer diameter (e.g., about 3, 4, 5, 6, 7 or 8 mm in diameter), among others. In some implementations, the counter fixation retainer and stress loop can be formed from the same length of wire. If desired, the main circumferential frame portion can be formed from a NiTi alloy wire of any suitable diameter or gauge. Moreover the frame can be formed from a plurality of wires of any desired materials that can be joined together using any desired techniques (e.g., brazing, soldering, welding, adhesives and the like).

In some embodiments, the prosthesis can include a first attachment point for receiving a first control rod of a delivery system, such as one disposed in a central region of the sub annular frame portion. Moreover, the prosthesis can further include a second attachment point for receiving a second control rod of the delivery system, such as one disposed in a central posterior region of the supra annular frame portion. If desired, the prosthesis can be configured to collapse away from the commissures when the first attachment point is urged away from the second attachment point. If desired, the prosthesis can include at least one guide eyelet for receiving a tether of a rail delivery system. In some embodiments, a stress coil can act as such an eyelet.

The disclosure further provides a prosthesis delivery system. The system includes a collapsed partial valvular prosthesis for implantation over a native mitral valve. The prosthesis includes a main circumferential frame having a supra annular frame portion for resting above the mitral annulus over a native posterior mitral leaflet and a sub annular frame portion for extending downwardly into a native left ventricle, the main circumferential frame being substantially covered by a curved membrane. The prosthesis further includes at least one deployable anchor attached to the main circumferential frame, the deployable anchor having a body formed from a wire material including at least one stress coil having at least one turn, the at least one stress coil being configured to urge the anchor outwardly to help hold the prosthesis in place upon deployment into a native mitral location. The delivery system contains the prosthesis mounted therein. The delivery system includes an elongate catheter having a proximal end and a distal end, and includes an elongate outer tubular member having a proximal end and a distal end, and an elongate tubular core longitudinally displaceable with respect to the elongate outer tubular member, the elongate tubular core including a non-traumatizing, rounded distal tip mounted thereon, the elongate tubular core assembly being configured to be advanced distally out of the elongate tubular outer member. The delivery system further includes a first elongate control rod disposed within and along the elongate outer tubular member having a proximal end and a distal end near the distal end of the elongate outer tubular member, the first elongate control rod being configured to be advanced distally out of the elongate outer tubular member after the distal tip is advanced distally out of the elongate outer tubular member, the first elongate control rod being removably connected to a first attachment point on the prosthesis. The delivery system also includes a second elongate control rod longitudinally displaceable with respect to the first elongate control rod, the second elongate control rod being disposed within and along the elongate outer tubular member having a proximal end and a distal end near the distal end of the elongate outer tubular member, the second elongate control rod being configured to be advanced distally out of the elongate outer tubular member after the distal tip is advanced distally out of the elongate outer tubular member, the second elongate control rod being removably connected to a second attachment point on the prosthesis, wherein the prosthesis is mounted within the elongate tubular outer member and can be advanced distally out of the elongate tubular outer member by advancing the first and second elongate control rods distally outwardly from the elongate tubular outer member.

If desired, the prosthesis can be configured to be expanded along a direction perpendicular to an axis defined by the delivery system by moving the distal ends of the first and second elongate control rods toward each other. If desired, the delivery system can further include a tether pre-routed through a portion of the at least one deployable anchor, wherein the at least one deployable anchor can be permitted to expand outwardly when the tether is loosened. In some embodiments, the delivery system can further include an anchor delivery member disposed within and along the elongate outer tubular member, the anchor delivery member including a torqueable proximal end and an anchor attached to a distal end of the anchor delivery member, the anchor delivery member being configured to be advanced distally outwardly from the distal end of the elongate outer tubular member after the prosthesis is advanced distally outwardly from the elongate outer tubular member.

The disclosure further provides a method for delivering a prosthesis, including providing a collapsed partial valvular prosthesis for implantation over a native mitral valve, including a main circumferential frame having a supra annular frame portion for resting above the mitral annulus over a native posterior mitral leaflet and a sub annular frame portion for extending downwardly into a native left ventricle, the main circumferential frame being substantially covered by a curved membrane, and at least one deployable anchor attached to the main circumferential frame, the deployable anchor having a body formed from a wire material including at least one stress coil having at least one turn, the at least one stress coil being configured to urge the anchor outwardly to help hold the prosthesis in place upon deployment into a native mitral location. The method further includes mounting the prosthesis within a delivery system, the delivery system including an elongate catheter having a proximal end and a distal end, having an elongate outer tubular member having a proximal end and a distal end, an elongate tubular core longitudinally displaceable with respect to the elongate outer tubular member, the elongate tubular core including a non-traumatizing distal tip mounted thereon, the elongate tubular core assembly being configured to be advanced distally out of the elongate tubular outer member, a first elongate control rod disposed within and along the elongate outer tubular member having a proximal end and a distal end near the distal end of the elongate outer tubular member, the first elongate control rod being configured to be advanced distally out of the elongate outer tubular member after the distal tip is advanced distally out of the elongate outer tubular member, the first elongate control rod being removably connected to a first attachment point on the prosthesis, and a second elongate control rod longitudinally displaceable with respect to the first elongate control rod, the second elongate control rod being disposed within and along the elongate outer tubular member having a proximal end and a distal end near the distal end of the elongate outer tubular member, the second elongate control rod being configured to be advanced distally out of the elongate outer tubular member after the distal tip is advanced distally out of the elongate outer tubular member, the second elongate control rod being removably connected to a second attachment point on the prosthesis, wherein the prosthesis is mounted within the elongate tubular outer member and can be advanced distally out of the elongate tubular outer member by advancing the first and second elongate control rods distally outwardly from the elongate tubular outer member. The method can further include advancing the distal end of the delivery system to a target location proximate a patient's mitral valve, advancing the elongate tubular core longitudinally and distally with respect to the elongate outer tubular member, and advancing the prosthesis distally with respect to the elongate outer tubular member by advancing the first and second elongate control rods distally with respect to the elongate outer tubular member.

The method can further include expanding the prosthesis laterally along a direction perpendicular to an axis defined by the delivery system by moving the distal ends of the first and second elongate control rods toward each other. The method can further include maneuvering the supra annular frame portion above the mitral annulus over the native posterior mitral leaflet and maneuvering the sub annular frame portion downwardly into the native left ventricle. The method can further include permitting the supra annular frame portion to expand laterally outwardly toward the commissures and to self-align within the mitral opening. The method can still further include releasing tension on a tether pre-routed through a portion of the at least one deployable anchor, wherein the at least one deployable anchor expands outwardly when tension on the tether is released.

If desired, the method can include advancing an anchor delivery member disposed within and along the elongate outer tubular member distally outwardly from the distal end of the elongate outer tubular member after the prosthesis is advanced distally outwardly from the elongate outer tubular member. Torque can be applied to a torqueable proximal end of the anchor delivery member to drive an anchor situated at a distal end of the anchor delivery member into cardiac tissue to hold the prosthesis in place.

In some implementations, the distal end of the delivery system can be advanced to a target location proximate a patient's mitral valve via a transapical approach through the left ventricle toward the left atrium, wherein the supra-annular frame portion of the prosthesis is oriented toward the distal end of the delivery system. In other embodiments, the distal end of the delivery system can be advanced to a target location proximate a patient's mitral valve via a percutaneous approach through the left atrium toward the left ventricle, wherein the sub-annular frame portion of the prosthesis is oriented toward the distal end of the delivery system.

The disclosure also provides a full valvular prosthesis for implantation over a native mitral valve. The prosthesis includes a main circumferential frame having a supra annular frame portion for resting above the mitral annulus over at least a native posterior mitral leaflet and a sub annular frame portion for extending downwardly into a native left ventricle, the main circumferential frame being substantially covered by a membrane, and at least one deployable anchor attached to the main circumferential frame, the deployable anchor having a body formed from a wire material including at least one stress coil having at least one turn, the at least one stress coil being configured to urge the anchor outwardly to help hold the prosthesis in place upon deployment into a native mitral location. The full prosthesis can be delivered to the mitral annulus or other anatomical target location using any technique described herein or in patent applications incorporated by reference herein.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 1A-1B are front and rear views, respectively, of an exemplary Intercommissural Prosthesis ("IP") system (for replacement of posterior leaflet) in an expanded configuration.

FIGS. 2A-2B are front and rear views, respectively, of the underlying framework of an exemplary intercommissural prosthesis system (for replacement of posterior leaflet) in an expanded configuration.

FIGS. 3A-3D are front, back, side and further back view with intercommisural wings in a closed position of an exemplary IP.

FIGS. 4A-4B illustrate an exemplary prosthesis in an expanded configuration with a variation of subvalvular multiple inversion anchor(s)/wing(s).

FIGS. 5A-5C illustrate an exemplary intercommissural prosthesis ("IP") mounted on a delivery system in a partially expanded condition wherein sub-annular wings are held in an undeployed condition by a tether (FIGS. 5A, 5B) and in a fully expanded condition after the tether is removed (FIG. 5C).

FIGS. 6A-6D illustrate an exemplary prostheses in partially expanded configurations (FIGS. 6A, 6C) with a tether holding retainers/anchors/wings in an undeployed condition and in a fully expanded configuration wherein the tethers are removed and the retainers/anchors/wings are deployed to hold the prosthesis in place.

FIGS. 8A-8B illustrate an exemplary IPDS with IP mounted thereon advanced to a native mitral site ready to be deployed with the sheath withdrawn to reveal a collapsed undeployed IP, wherein FIG. 8A illustrates a transapical approach and FIG. 8B illustrates a Left Atrial percutaneous approach.

FIGS. 9A-9B illustrate a further sequence in deployment of the IPDS's illustrated in FIGS. 8A-8B, wherein the intercommissural self-alignment supra-annular frame is expanded by moving the distal delivery control rod with respect to the proximal delivery control rod, wherein FIG. 9A illustrates the transapical approach and FIG. 9B illustrates the Left Atrial approach.

FIGS. 10A-10B illustrate an exemplary IP in an expanded condition after delivery to a native posterior mitral site, wherein FIG. 10A is a top view showing relative location of the anterior mitral valve leaflet, and FIG. 10B presents a post necropsy view.

FIGS. 11A-11B illustrate an exemplary Intercommissural Prosthesis ("IP") in expanded position and placed in a mitral annulus, wherein FIG. 11A illustrates relative positioning of the native anterior leaflet in an open condition, and wherein FIG. 11B illustrates the anterior leaflet is a closed condition against the prosthesis.

FIG. 14A illustrates an exemplary full replacement prosthesis system in accordance with the disclosure, side view.

FIG. 14B illustrates an exemplary full replacement prosthesis system in accordance with the disclosure, front view.

FIG. 14C illustrates an exemplary full replacement prosthesis system in accordance with the disclosure, further side view.

FIG. 15A illustrates an exemplary full replacement prosthesis system in accordance with the disclosure.

FIG. 15B illustrates a further exemplary full replacement prosthesis system in accordance with the disclosure.

DETAILED DESCRIPTION

Figure 7A:
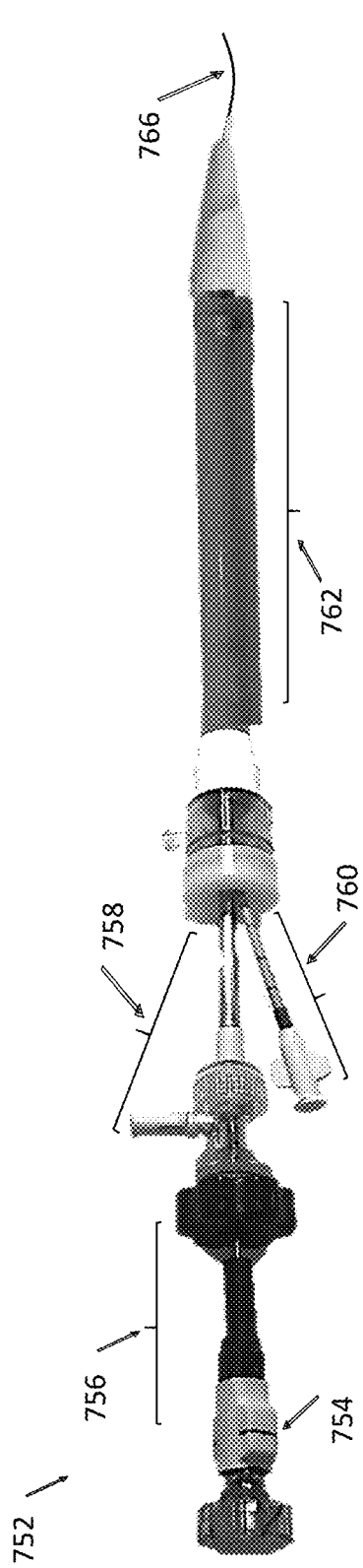
FIGS. 7A-7B illustrate aspects of an exemplary Intercommissural Prosthesis Delivery System (IPDS), ready to be delivered to site with compressed prosthesis mounted therein (FIG. 7A) and ready to attached a prosthesis to be loaded into the delivery system (FIG. 7B).

Reference will now be made in detail to the present preferred embodiments of the disclosure, examples of which are illustrated in the accompanying drawings. The method and corresponding steps of the disclosed embodiments will be described in conjunction with the detailed description of the system.

Exemplary embodiments provide systems, devices and methods for repairing or replacing elements of the mitral valve. Exemplary elements of the valve prosthesis include the device frame, prosthetic posterior mitral leaflet equivalent and elements to prevent or reduce abnormal prolapse of the native anterior mitral leaflet during systole, as well a full mitral replacement prosthesis. Exemplary methods of implanting the valve prosthesis include direct open surgical placement, minimally invasive surgical placement either with or without the use of cardiopulmonary bypass, and totally catheter based implantation. Exemplary methods for maintaining the valve prosthesis in the preferred mitral annular location include external compression, compression following percutaneous deliver, or rail or suture guided implantation and seating with subsequent active or passive fixation of the valve prosthesis based upon the rail or suture guides.

In some implementations, the disclosure provides a partial valvular prosthesis for implantation over a native mitral valve. The prosthesis includes a main circumferential frame having a supra annular frame portion for resting above the mitral annulus over a native posterior mitral leaflet and a sub annular frame portion for extending downwardly into a native left ventricle. The main circumferential frame is preferably substantially covered by a curved membrane. The prosthesis also includes at least one deployable anchor attached to the main circumferential frame, the deployable anchor having a body formed from a wire material including at least one stress coil having at least one turn, the at least one stress coil being configured to urge the anchor outwardly to help hold the prosthesis in place upon deployment into a native mitral location.

For purposes of illustration, and not limitation, embodiments of a partial prosthesis and aspects thereof are illustrated in the embodiments of FIGS. 1-13. Aspects of a full prosthesis are illustrated in FIGS. 14-15. As used herein, the last two digits of a reference number correspond to similar elements in the Figures. For example, element "108" in FIG. 1 is similar to element 208 in FIG. 2.

FIGS. 1A-1B are front and rear views, respectively, of an exemplary Intercommissural Prosthesis ("IP") system (for replacement of posterior leaflet) in an expanded configuration. In FIGS. 1A-1B, 102 refers to coaptation depth-supra-annular portion, 104 refers to intercommissural self-alignment expansion fixation, 106 refers to frame depth in LV-sub-annular portion, 108 refers to counter fixation wings-supra-annular portion, 110 refers to anchor-free fixation, intercommissural-sub-annular portion, 112 refers to porcine pericardial tissue membrane, 114 refers to main saddle-shaped frame, 116 refers to the base of the sub-annular portion and attachment mechanism point/location for delivery, 118 refers to attachment mechanism point/location for delivery, 120 refers to subvalvular inversion wing(s)/anchors/retainers which are spring loaded and configured to urge outwardly and upwardly against the mitral annulus and/or ventricular walls, 122 refers to tissue drape attached to the back of 114, which can act to control paravalvular leaks. The prosthesis is illustrated including a membrane, in this case, a porcine tissue membrane as set forth above.

By way of further illustration, FIGS. 2A-2B are front and rear views, respectively, of the underlying framework of an exemplary intercommissural prosthesis system (for replacement of posterior leaflet) in an expanded configuration. Accordingly, 224 refers to a commissure expanded loop portion to allow for better positioning and coaptation to native anterior leaflet. As is evident from the figure, the frame if principally formed by two loops that overlap along their extent except for the lateral expanded loop portions, thereby defining crescent shaped lateral framework structures on the prosthesis. Also illustrated are eyelets/coils 226 (or stress coils or loops), which are formed into various portions of the prosthesis to minimize stress and to optionally provide guide eyelets for rail fixation techniques. Such coils can be provided with a plurality of turns, thereby permitting the sub-annular anchors to be retracted by a tether, as illustrated herein. Anchors/retainers above and below the mitral annulus can be formed from the same segment of wire, if desired, and include one or more stress loops (stress distribution loops) formed therein. The stress distribution loops distribute stress across the wire, which can be particularly useful in the case of NiTi materials, as such materials can be brittle and prone to fracture when bent excessively.

FIGS. 3A-3D are front, back, side and further back view with intercommisural wings in a closed position of an exemplary IP. This embodiment differs from the embodiment of FIGS. 1-2 in that the base of the sub-annular portion and attachment mechanism point/location for delivery 316 and the subvalvular inversion wing(s)/anchors/retainers 320 are combined, resulting in the plane of the membrane of the prosthesis being fully pulled back and brought back and under the mitral annulus.

FIGS. 4A-4B illustrate an exemplary prosthesis in an expanded configuration with a variation of subvalvular multiple inversion anchor(s)/wing(s). In FIG. 4A, 430 refers to a first arrangement of subvalvular multiple inversion wings. In FIG. 4B, 432 refers to a second arrangement of subvalvular multiple inversion anchors/wings. As will be appreciated, any desired suitable number of deployable anchors/wings can be used.

FIGS. 5A-5C illustrate an exemplary intercommissural prosthesis ("IP") mounted on a delivery system in a partially expanded condition wherein sub-annular wings are held in an undeployed condition by a tether (FIGS. 5A, 5B) and in a fully expanded condition after the tether is removed (FIG. 5C). Accordingly, 532 refers to the illustrated variation of subvalvular multiple inversion anchor(s)/wing(s), 522 refers to a drape, 524 refers to the commissure expanded loop to allow for better positioning and coaptation to the native anterior leaflet, the tissue drape 522 is attached to the back of a redundancy feature to control paravalvular leaks, 536 refers to the eyelet/coil placed along the prosthesis to minimize stresses in the frame, 538 refers to the delivery system distal end, 540 refers to supra-annular expansion loops, 542 refers to the tether, which holds the sub-annular wings/anchors 532 closed allowing simplified loading, individual repositioning and final deployment.

FIGS. 6A-6D illustrate an exemplary prostheses in partially expanded configurations (FIGS. 6A, 6C) with a tether holding retainers/anchors/wings in an undeployed condition and in a fully expanded configuration wherein the tethers are removed and the retainers/anchors/wings are deployed to hold the prosthesis in place. Specifically, 644 refers to a variation of intercommissural fixation sub-annular, 646 refers to variation of intercommissural fixation sub-annular, 612 refers to porcine pericardial tissue membrane, 614 refers to the main saddle-shaped frame, 616 refers to the base of the sub-annular and attachment mechanism for delivery, 648 refers to a variation of subvalvular inversion anchor(s)/wing(s), 650 refers to a variation of subvalvular inversion anchor(s)/wing(s), 622 refers to a drape, and 642 refers to a tether.

Figure 7B:
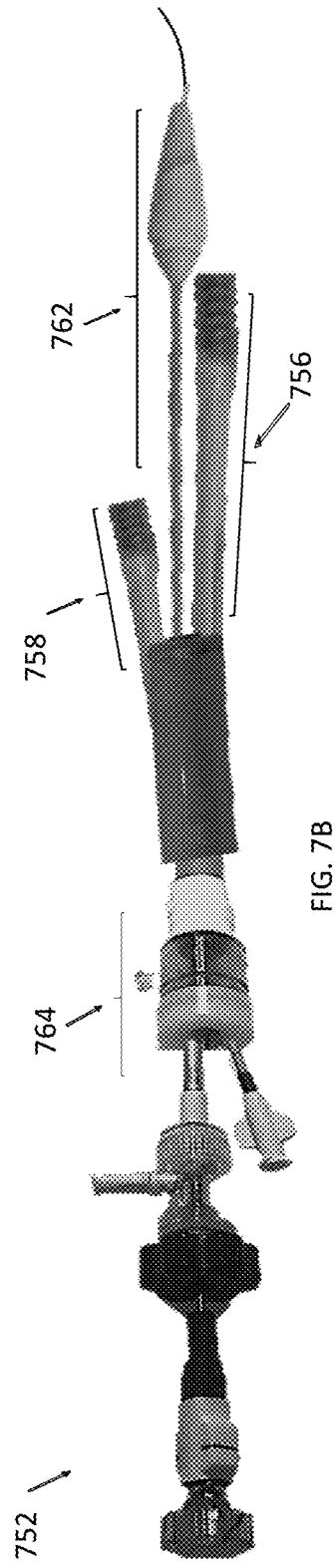

FIGS. 7A-7B illustrate aspects of an exemplary Intercommissural Prosthesis Delivery System (IPDS) 752, ready to be delivered to site with compressed prosthesis mounted therein (FIG. 7A) and ready to attached a prosthesis to be loaded into the delivery system (FIG. 7B). Accordingly, 754 refers to a back end mechanism for holding the tether, 756 refers to a second shaft back and front end with an injection port and attachment mechanism to the prosthesis, 758 refers to a first shaft back and front end with injection port and attachment mechanism to prosthesis, 760 refers to a third shaft back and with soft front end, 762 refers to a main Catheter, 764 refers to a main hemostasis hub with injection port, and 766 refers to a guidewire access.

FIGS. 8A-8B illustrate an exemplary IPDS with IP mounted thereon advanced to a native mitral site ready to be deployed with the sheath withdrawn to reveal a collapsed undeployed IP, wherein FIG. 8A illustrates a transapical approach and FIG. 8B illustrates a Left Atrial percutaneous approach. In FIGS. 8, 868 and 870 refer to native mitral valve commissures, 872 refers to a native anterior leaflet, 874 refers to a native posterior leaflet, 876 refers to a collapsed prosthesis in position for transapical access, 878 refers to a second shaft front end, and 880 refers to a first shaft front end.

Figure 9B:
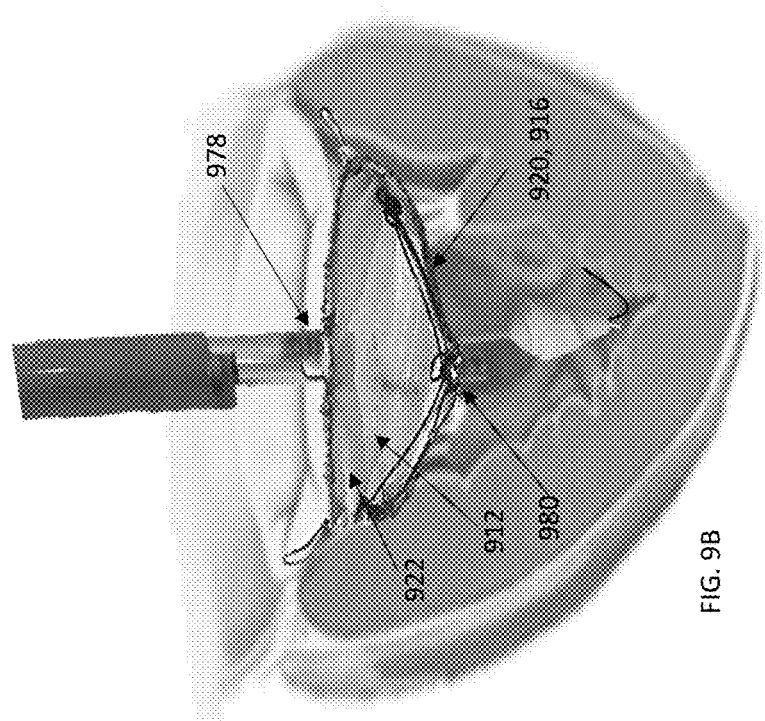
Figure 9A:
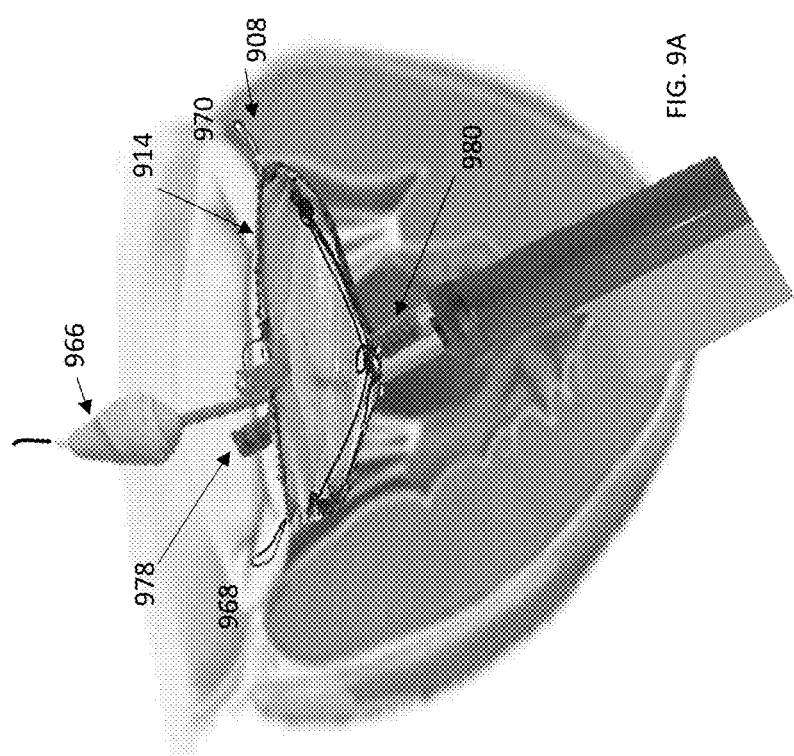

FIGS. 9A-9B illustrate a further sequence in deployment of the IPDS's illustrated in FIGS. 8A-8B, wherein the intercommissural self-alignment supra-annular frame is expanded by moving the distal delivery control rod with respect to the proximal delivery control rod, wherein FIG. 9A illustrates the transapical approach and FIG. 9B illustrates the Left Atrial approach, wherein 968 and 970 refer to native mitral valve commissures, 978 refers to the second shaft being released, and 980 refers to the first shaft front end.

FIGS. 10A-10B illustrate an exemplary IP in an expanded condition after delivery to a native posterior mitral site, wherein FIG. 10A is a top view showing relative location of the anterior mitral valve leaflet, and FIG. 10B presents a post necropsy view, wherein 1068 and 1070 refer to native mitral valve commissures, 1072 refers to the native anterior leaflet, 1074 refers to the native posterior leaflet, and 1082 refers to an exemplary partial replacement (posterior only) prosthesis deployed.

Figures 11A, 11B:
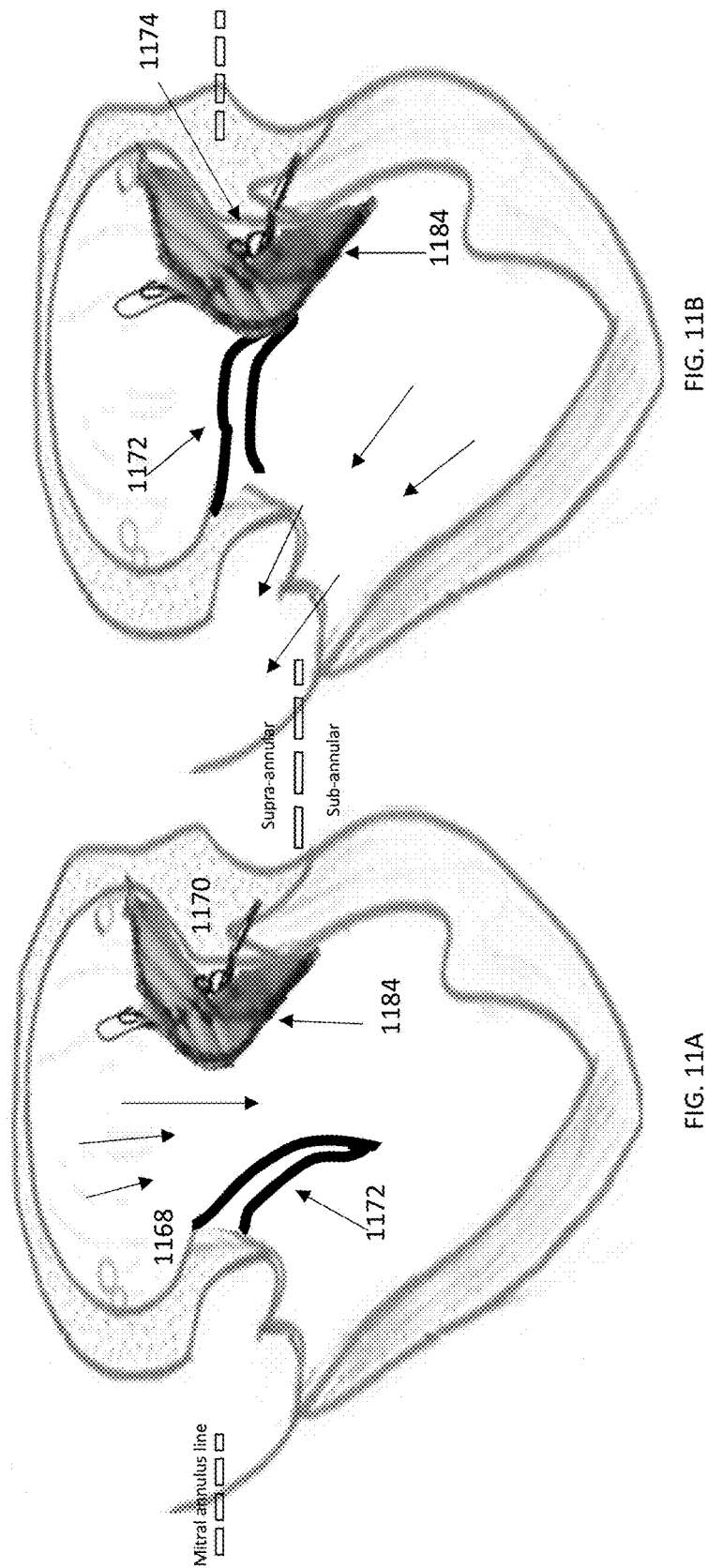

FIGS. 11A-11B illustrate an exemplary Intercommissural Prosthesis ("IP") in expanded position and placed in a mitral annulus, wherein FIG. 11A illustrates relative positioning of the native anterior leaflet 1172 in an open condition, and wherein FIG. 11B illustrates the anterior leaflet 1172 is a closed condition against the prosthesis, wherein 1184 refers to a partial replacement (posterior only) prosthesis deployed.

Figure 12B:
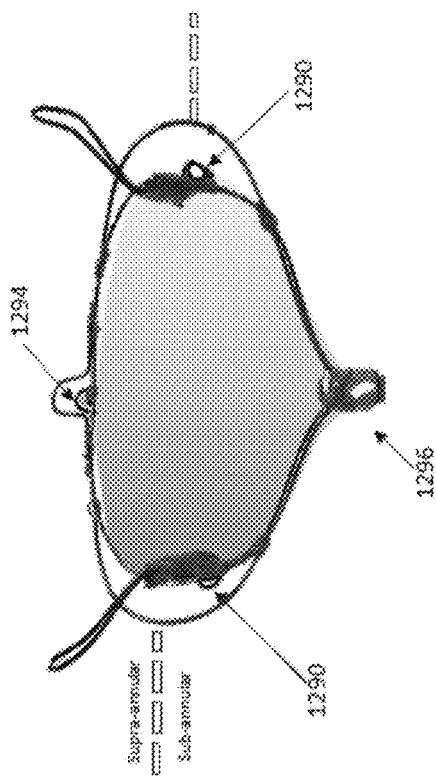
FIG. 12B illustrates a back view of an exemplary IP configured to be delivered by rail fixation with eyelets for rail fixation, an inter commissural eyelet, a main frame central eyelet, and a sub-annular base eyelet.
Figure 12A:
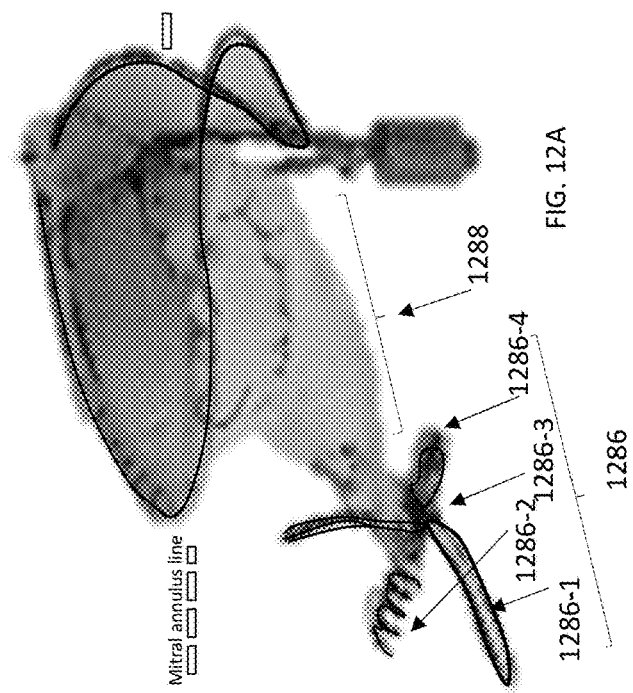
FIG. 12A illustrates an exemplary Intercommissural Prosthesis ("IP") in an expanded condition with an adjustable drape, and an on demand feature for facilitating rail fixation, expandable wings, and a screw anchor attached to the adjustable drape.

FIG. 12A illustrates an exemplary Intercommissural Prosthesis ("IP") in an expanded condition with an adjustable drape, and an on demand feature for facilitating rail fixation, expandable wings, and a screw anchor attached to the adjustable drape. Specifically, FIG. 12A illustrating an exemplary Intercommissural Prosthesis System in an expanded position with adjustable drape 1288, and an "on demand" version of rail fixation 1286, expandable wings 1286-1, screw anchor 1286-2, attachment of the on demand fixation to the adjustable drape. FIG. 12B illustrates an exemplary prosthesis system in an expanded state with eyelets for rail fixation, inter commissural eyelet 1290, main frame center eyelet 1292, and sub-annular base eyelet 1294.

Figure 13B:
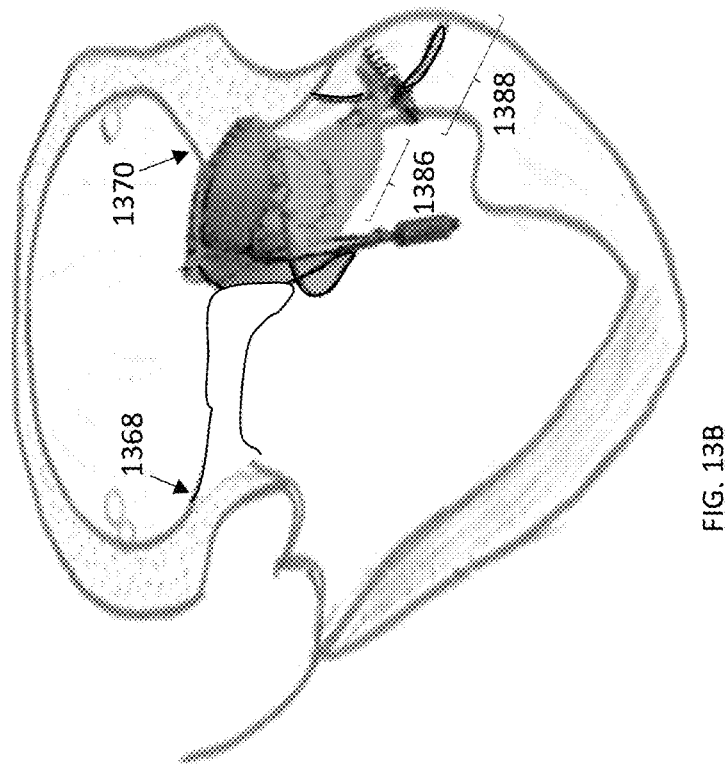
FIG. 13B illustrates the IPDS of FIG. 13A after implantation.
Figure 13A:
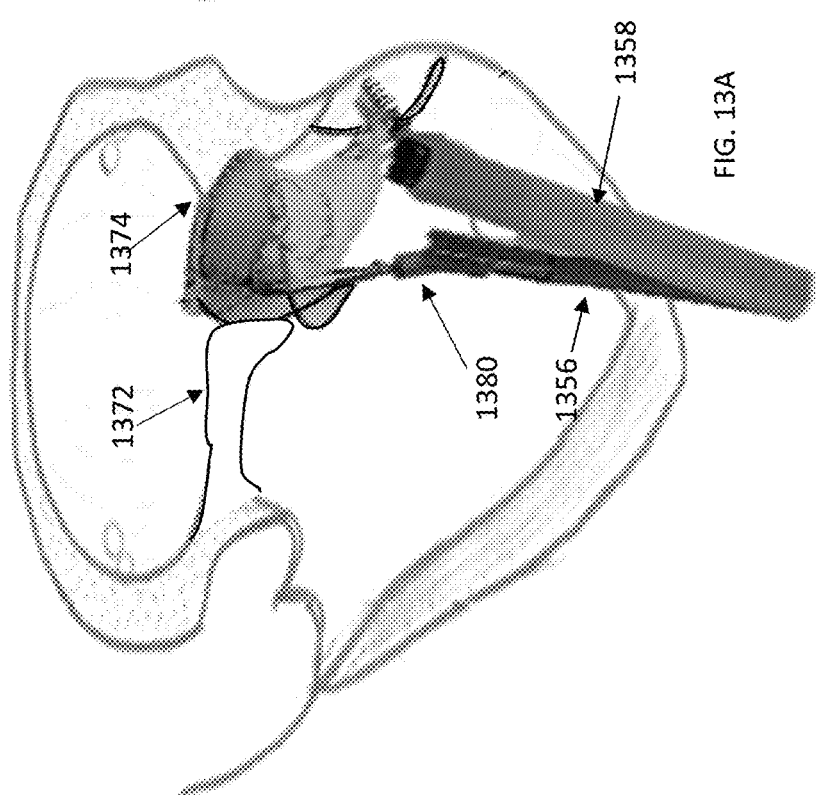
FIG. 13A illustrates an exemplary IPDS advanced to a native mitral site via a transapical approach (side view).

FIG. 13A illustrates an exemplary IPDS advanced to a native mitral site via a transapical approach (side view) and FIG. 13B illustrates the IPDS of FIG. 13A after implantation. Both prosthesis and on demand fixation 1388 are delivered to the site at the same time in this embodiment. While the base 1380 of prosthesis, and on demand fixation 1388, are held and ready to be deployed, the prosthesis main frame supra annular is deployed and self aligned to the commissures 1368 and 1370. Then, the on demand fixation 1388 is placed to the LV wall and/or posterior sub-annulus. After confirming the essential signs (e.g., under fluoroscopy) the prosthesis base is released. Prior to full release the system can be retrieved. While sutures can be used to hold devices depicted herein in place, this is not necessary. Also, while implantation using surgical techniques with a bypass machine are possible, it is preferred to deliver and implant the prosthesis and adjust its positioning while the heart is still beating under visualization (e.g., fluoroscopy) to ensure acceptable coaptation between the native anterior leaflet and the prosthesis.

FIG. 14A illustrates an exemplary full replacement prosthesis system in accordance with the disclosure, side view. FIG. 14B illustrates an exemplary full replacement prosthesis system in accordance with the disclosure, front view. FIG. 14C illustrates an exemplary full replacement prosthesis system in accordance with the disclosure, further side view. Both sub-annular loops 1497 and supra-annular loops 1491 and 1493 are used for attaching the full tissue valve and support of the full prosthesis to mitral valve annulus. FIG. 14A-14C illustrate a version of the on-demand anchors 1499, in that the prosthesis and the on demand anchors are delivered to the site. In FIGS. 14A-14C, 1495 refers to the sub-annular base. After full deployment of the prosthesis the on demand anchors 1499 are deployed. The system can be used for both Transapical and Left Atrium approaches. It will be appreciated that all variations of rail fixation from this application and others incorporated by reference herein can be used to deliver the illustrated full prosthesis as well as to fixate the prosthesis.

FIG. 15A illustrates an exemplary full replacement prosthesis system in accordance with the disclosure. FIG. 15b illustrates a further exemplary full replacement prosthesis system in accordance with the disclosure. It will be appreciated that the embodiment of FIG. 15B can utilize the delivery system illustrated in FIGS. 7A and 7B. The system can be deployed both by transapical and Left Atrium approaches, in that the prosthesis is inverted for one approach versus the other by attaching the prosthesis to the opposing control rods. This prosthesis is also repositionable and retrievable prior to full release.

All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The methods and systems of the present disclosure, as described above and shown in the drawings, provide for improved techniques for treating mitral valves of patients. It will be apparent to those skilled in the art that various modifications and variations can be made in the devices, methods and systems of the present disclosure without departing from the spirit or scope of the disclosure. Thus, it is intended that the present disclosure include modifications and variations that are within the scope of the subject disclosure and equivalents.

What is claimed is:

1. A valvular prosthesis that is implantable over a native valve annulus, comprising:
   a) a main circumferential frame, substantially covered by a curved membrane, having a supra annular frame portion and a sub annular frame portion, wherein, upon deployment into a native valve location, the supra annular frame portion rests above a valve annulus over a native valve leaflet and the sub annular frame portion extends downwardly;
   b) at least one deployable spring-loaded anchor attached to the main circumferential frame, wherein the at least one deployable anchor includes:
   an elongate body formed from a nickel-titanium alloy shape memory wire material formed into an elongate loop having a first end and a second free end, the free end having a rounded tip, and being configured to rest against native cardiac tissue; and
   at least one coil-shaped stress relief loop formed from said nickel-titanium alloy shape memory wire connecting the main circumferential frame to the first end of the elongate body, said at least one coil-shaped stress relief loop being configured and arranged to urge said elongate body to swing outwardly along an arcuate path about said at least one coil-shaped stress relief loop toward native cardiac tissue, wherein said at least one coil-shaped stress relief loop is configured to deflect and absorb bending stress along its length when said elongate body is forced inwardly to permit said elongate body of said at least one deployable anchor to be fully collapsed without fracturing said nickel-titanium alloy shape memory wire;
   c) at least one guiding tether, wherein said at least one coil-shaped stress relief loop is configured and arranged to serve as a guide eyelet configured and arranged to receive the at least one guiding tether, and wherein said at least one guiding tether is configured and arranged such that when received by the at least one coil-shaped stress relief loop, said at least one guiding tether can hold the at least one deployable anchor in an undeployed position;
   d) a plurality of counter fixation retainers disposed on the supra annular frame portion of the prosthesis, wherein at least two of the counter fixation retainers are configured and arranged to engage a native tissue wall proximate opposing native commissures,
   wherein the prosthesis is configured and arranged to expand outwardly toward the commissures of the valve during implantation and is configured and arranged to self-align in the valve opening.

2. The prosthesis of claim 1, wherein said free end of said at least one deployable anchor is configured to deploy against a portion of a native left ventricular site.

3. The prosthesis of claim 2, wherein said at least one deployable anchor includes at least two deployable anchors said at least two deployable anchors being configured and arranged to self-expand against the left ventricle under force applied by said coil-shaped stress relief loops to help hold the prosthesis in place.

4. The prosthesis of claim 3, wherein said at least two deployable anchors includes three deployable anchors, said three deployable anchors being configured and arranged to self-expand against the left ventricle to help hold the prosthesis in place.

5. The prosthesis of claim 4, wherein two of the three deployable anchors are configured and arranged to self-expand laterally into the ventricle near the middle of the mitral annulus, and the third deployable anchor is configured and arranged to self-expand toward a location underneath a central region of the posterior mitral annulus.

6. The prosthesis of claim 3, wherein the main circumferential frame of the prosthesis includes a third deployable anchor that is configured and arranged to self-expand toward a location underneath a central region of the posterior mitral annulus.

7. The prosthesis of claim 6, wherein the curved membrane is stretched over the third deployable anchor.

8. The prosthesis of claim 7, wherein the curved membrane of the prosthesis defines a curved plane that stretches from above the mitral annulus proximate the periphery of the mitral annulus and curves downwardly into the left ventricle and bends upwardly to contact the underside of a central posterior region of the mitral annulus.

9. The prosthesis of claim 1, wherein the main circumferential frame includes at least one perimeter wire loop that traverses the perimeter of the curved membrane.

10. The prosthesis of claim 9, wherein the at least one perimeter wire loop forms a saddle shape when the prosthesis is deployed to match a saddle shape of a native mitral annulus in which the prosthesis is configured to be implanted.

11. The prosthesis of claim 9, wherein the main circumferential frame includes an outer perimeter structural wire attached to an inner circumferential loop, wherein the at least one deployable anchor is attached to the inner circumferential loop.

12. The prosthesis of claim 11, wherein the at least one coil-shaped stress relief loop is disposed in a sub annular location.

13. The prosthesis of claim 11, wherein the outer perimeter structural wire extends outwardly laterally beyond the inner circumferential loop to form crescent shaped frames on each side of the prosthesis to facilitate positioning of the prosthesis upon installation.

14. The prosthesis of claim 1, wherein one of the counter fixation retainers and the coil-shaped stress relief loop are formed from the same length of nickel-titanium alloy shape memory wire.

15. The prosthesis of claim 1, wherein the main circumferential frame is formed from nickel-titanium alloy shape memory wire.

16. The prosthesis of claim 1, further comprising a first attachment point disposed in a central region of the sub annular frame portion and configured to removably receive a first control rod of a delivery system.

17. The prosthesis of claim 16, further comprising a second attachment point disposed in a central posterior region of the supra annular frame portion and configured to removably receive a second control rod of the delivery system.

18. The prosthesis of claim 1, wherein the prosthesis is shaped to fit into a native tricuspid valve annulus.

19. The prosthesis of claim 1, wherein the prosthesis is shaped to fit into a native mitral valve annulus.

20. The prosthesis of claim 1, wherein the at least one deployable anchor can be permitted to expand outwardly when the at least one guiding tether is loosened.

* * * * *